(12) United States Patent
Lau et al.

(10) Patent No.: US 6,431,719 B1
(45) Date of Patent: Aug. 13, 2002

(54) DYNAMIC DISPLAY NIGHT LIGHT

(75) Inventors: Shek Fai Lau, Foster City; Edward C. McKinney, Jr., San Rafael; Richard J. Thalheimer, San Francisco, all of CA (US)

(73) Assignee: Sharper Image Corporation, San Francisco, CA (US)

( * ) Notice: Subject to any disclaimer, the term of this patent is extended or adjusted under 35 U.S.C. 154(b) by 0 days.

(21) Appl. No.: 09/668,594

(22) Filed: Sep. 22, 2000

(51) Int. Cl.[7] ............................................. F21V 33/00
(52) U.S. Cl. ...................... 362/95; 362/802; 362/800; 362/226; 362/29
(58) Field of Search .............................. 362/27, 29, 95, 362/800, 802, 224, 231; 446/485, 484, 219; 315/800

(56) References Cited

U.S. PATENT DOCUMENTS 3,968,355 A * 7/1976 Smallegan ................... 240/2
4,161,018 A * 7/1979 Briggs et al. ............... 362/104
4,338,547 A * 7/1982 McCaslin .................... 315/312
5,871,271 A * 2/1999 Chien ......................... 362/106
6,183,100 B1 * 2/2001 Suckow et al. ............... 362/35

* cited by examiner

Primary Examiner—Sandra O'Shea
Assistant Examiner—Anabel Ton
(74) Attorney, Agent, or Firm—Fliesler Dubb Meyer & Lovejoy, LLP

(57) ABSTRACT

A self-contained night light is disposed in a housing containing spaced-apart male AC prongs the mate with an AC socket. The housing contains an array of differently colored, preferably light emitting diode. Light sources that can dynamically output different patterns of differently colored light in response to drive signals. A microcontroller executes a sequence of instructions causing the controller to output different sequences of signals that are coupled to a driver unit that drives the light sources. The result is that the array dynamically produces different patterns of differently colored light. A user operable control allows a viewer to "freeze" any desired pattern of light, such that until reset, the night light will continue to output a static pattern of colors. The night light may include a manual or light-sensing ON/OFF switch.

20 Claims, 2 Drawing Sheets

DYNAMIC DISPLAY NIGHT LIGHT

FIELD OF THE INVENTION

The invention relates generally to night lights that plug into household AC current, and more particularly to providing a nightlight that outputs a dynamic light display that is both entertaining and soothing to a viewer.

BACKGROUND OF THE INVENTION

Night lights are commonly found in every household. Essentially they are small perhaps 15 Watt AC filament lamps that plug directly into a wall mounted AC outlet. The lamp outputs light (and heat) for as long as the lamp is turned on. While such lights can adequately provide a comforting level of light, they do little else. Although small children may find such lights reassuring, the lights themselves do little to sooth children and others viewing the light.

What is needed is a nightlight that can entertain and sooth a viewer, as well as merely output light. Preferably such a night light should output a display of light that is dynamic but can be user-frozen in a designed light pattern.

The present invention provides such a nightlight.

SUMMARY OF THE PRESENT INVENTION

The present invention provides a night light that includes a housing adapted to plug directly into a household type AC socket, an array of light emitters, an AC:DC voltage converter, associated electronics disposed within the housing, and a light diffuser to soften output from the light array.

Preferably the light array comprises several differently colored light emitting diodes (LEDs) that are driven by electronics within the housing such that the array output, as viewed through the light diffuser, is a dynamically changing pattern of light. The displayed light patterns vary smoothly and continuously from monochrome to different color combinations of light, with the cycle repeating over a cycle period that may be sixty seconds or so in length. Preferably the electronics includes a microcontroller unit that executes a sequence of instructions causing a light driver unit to switch on various of the light emitters during various portions of a pattern cycle. During the cycle period, a user may at any time activate a switch to "freeze" an especially attractive pattern of output light. The "frozen" light pattern will be displayed until the user again activates that switch (or the night light is turned off or otherwise disconnected from the source of operating potential). The viewer may later activate the same switch, which "unfreezes" the output light pattern, and permits the electronics to again drive the LEDs to produce a continuously varying pattern of light that is gradually modulated in color and in intensity. Preferably a red LED, a blue LED, and a green LED are used, and the drive electronics preferably is controlled by a microcontroller (or equivalent) that determines the light patterns output by the present invention.

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 1:
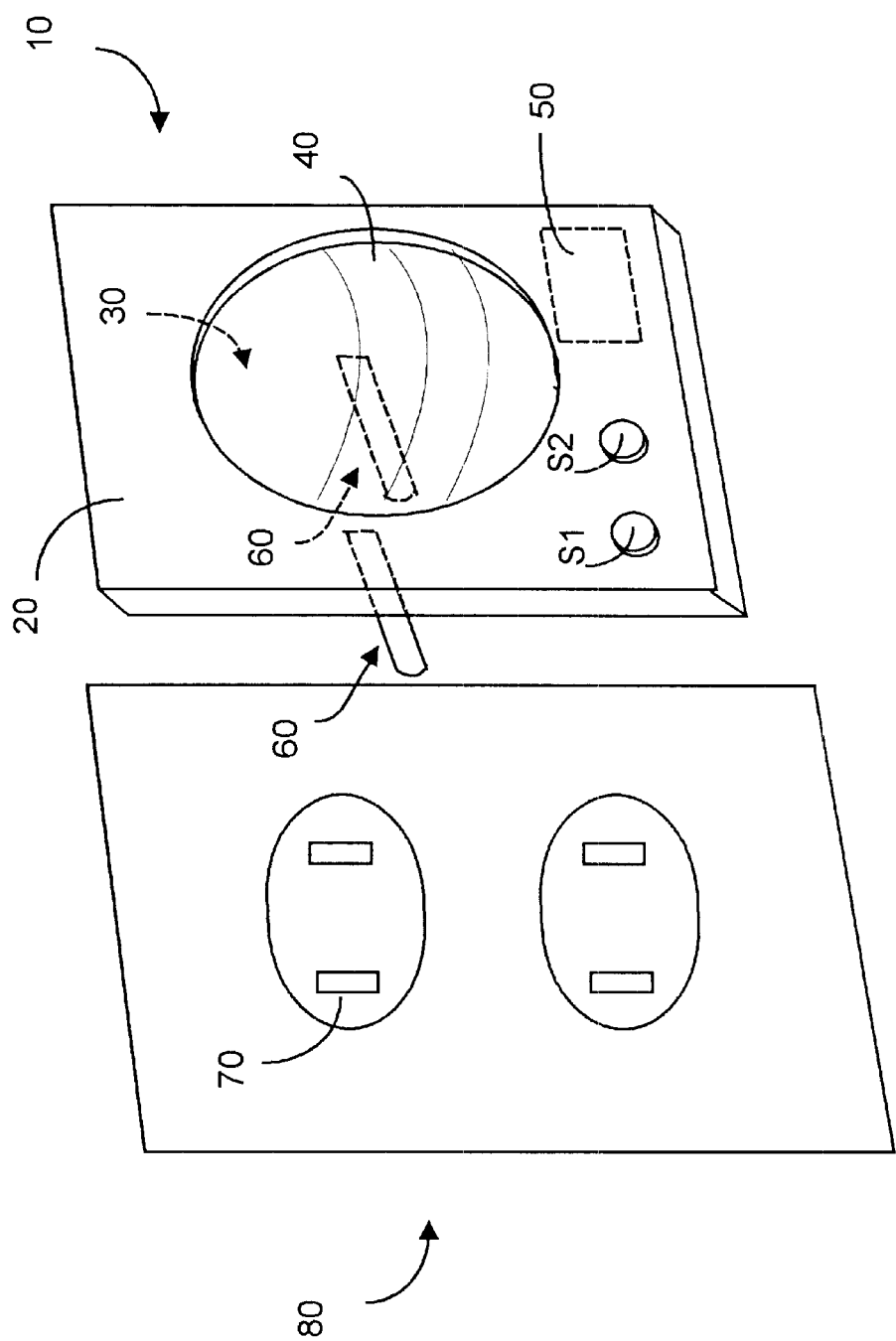
FIG. 1 is a perspective view of a preferred implementation of the present invention.

FIG. 1 is a perspective view of a night light 10, according to the present invention. Night light 10 includes a preferably plastic housing 20 with which an array 30 of light sources is disposed, with emitted light viewable through a preferably somewhat translucent element 40, for example a diffusive plastic lens. In the preferred embodiment, light array 30 includes several light emitting diodes (LEDs). Housing 20 also includes electronics 50, which includes an AC:DC power converter, and components to control and drive the LEDs within LED array 30. In the preferred embodiment, night light 10 includes two spaced-apart male plugs prongs 60 that mate with and plug directly into sockets 70 in a typically wall-mounted AC receptacle 80. Housing 20 also includes a switch S1 that permits a user to "freeze" a particular light output pattern at any time, or to "unfreeze" a previously frozen display pattern of light output by array 30. When night light 10 is plugged into receptacle 80, electronics 50 is energized and varying patterns of light will be output from the LED array 30 until switch S1 is pressed by a user.

When S1 is pressed or otherwise activated, the dynamic pattern of light output is frozen, and the night light will display a static pattern that was selected by the user at the moment S1 was activated. This static pattern will remain as the display until S1 is later re-activated (or night light 10 is turned OFF or otherwise de-activated). If desired, system 10 could also include an ON/OFF switch and/or an ambient light sensor S2 such that night light 10 could at all times remain plugged into receptacle 80, yet would only output light when the unit was switched ON, or when sensed ambient light was somewhat dark.

Figure 2:
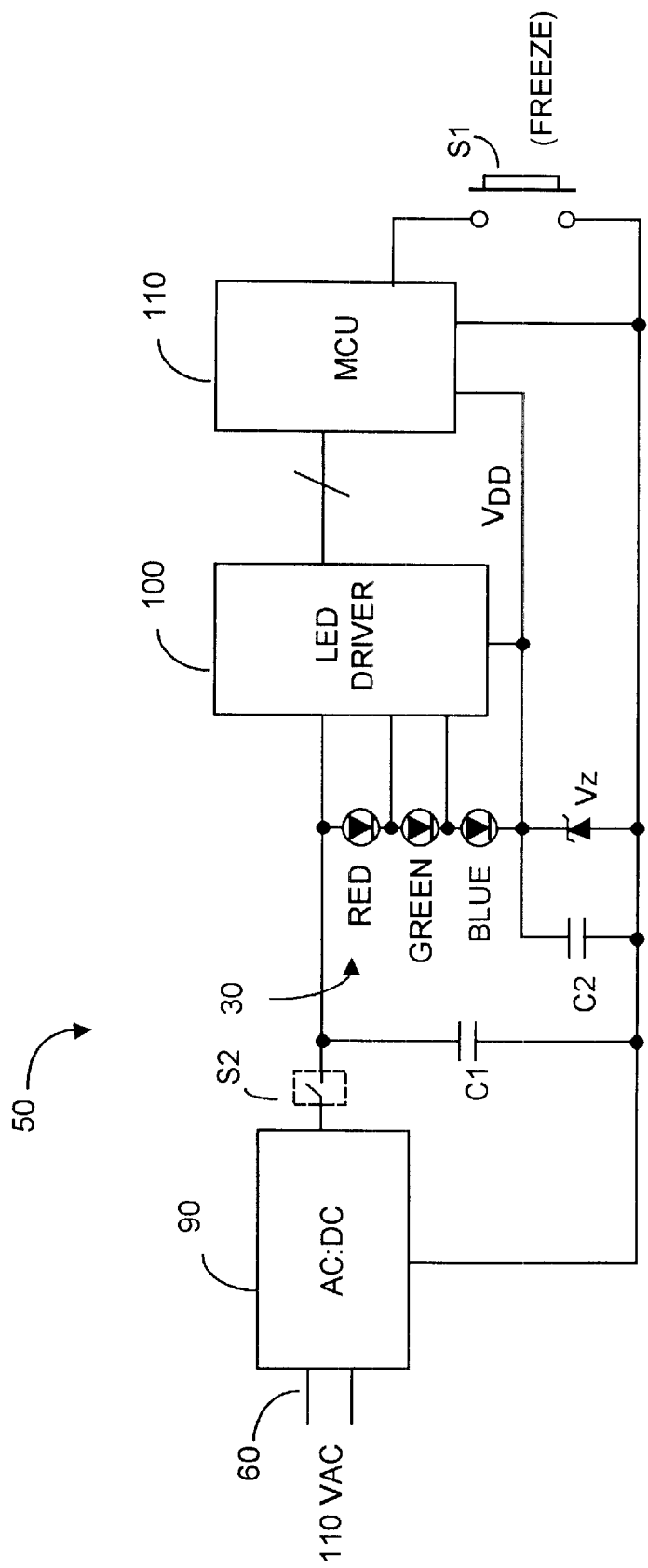
FIG. 2 is a generalized block diagram of the electronic circuitry used in the present invention.

FIG. 2 is a block diagram showing electronics 50 and associated components comprising night light 10. Spaced-apart male prongs 60 bring raw 110 VAC into system 10 when the night light is plugged into AC receptacle 80. An AC:DC rectifier and voltage conditioner unit 90 converts the raw AC voltage into DC voltage, which DC voltage (perhaps about 15 VDC) is somewhat filtered by capacitor C1. The design and implementation of such AC:DC converters is well known to those skilled in the relevant art and need not be described in detail.

In the preferred embodiment, LED array 30 includes three separate LEDs: a red LED, a green LED, and a blue LED, so labeled in FIG. 2. Each LED may be driven independently of each other LED by an appropriate logic high or low state provided by an LED driver 100. In the preferred embodiment, the three differently colored LEDs are series-connected, and the voltage at the bottom of the series stack is established by a Zener diode Vz, whose relatively constant voltage VDD is provided as operating potential to LED driver 100 and to a microcontroller unit (MCU) 110. MCU 110 preferably is programmed by burning one or more mask layers to carry out a set of instructions that have the effect of controlling LED driver 100 to drive the LED array 30 in a desired sequence of light patterns. LED drivers and MCU units are well known to those skilled in the art of circuit design, and further details are therefor deemed unnecessary. A capacitor C2 tends to filter out noise components in the Zener diode output level. The lower node of the Zener diode acts a ground node for electronics 50.

As noted switch S2 may be a conventional mechanical ON/OFF switch that a user could press or otherwise engage, or S2 may be a light sensor that senses ambient light through diffuser 40. If sensor S2 detects a darkened ambient light condition, S2 will essentially close circuit, and if S2 detects a bright ambient light condition, S2 will open circuit. Mechanical switches and/or light sensor switches S2 are know to those skilled in the art. As shown in FIG. 2, preferably LED driver 100 operates under control of MCU 110, which (unless interrupted by switch S1) will cycle through a sequence of programmed instructions (shown as 120) during a cycle period of perhaps sixty seconds or so. Multiple connections between MCU 110 and LED driver 100 cause driver 100 to step through various combinations of driver signals that are coupled to the LEDs comprising array 30.

For example, under control of MCU 110, LED driver 100 may cause only the blue LED to be on, or to be on for some fraction of a cycle period. Alternatively only the green or the red LED might be on for some fraction of a cycle period, e.g., a typically several second period over which a pattern of light output by array 30 occurs and then starts to repeat. It is understood that MCU 110 may cause LED driver 100 to switch more than one LED on simultaneously, and indeed duty cycle to each LED may differ. For example, one might drive the red LED with a higher duty cycle than the green and blue LEDs such that red is the predominant color as viewed through diffuser 40 by a user. While FIG. 2 depicts an array 30 comprising a series connection of light sources, if desired parallel-coupled light sources could be used instead (or in addition).

In practice MCU 110 will have been preprogrammed with at least one instruction set 120 to output a continuously changing pattern of MCU signals. These signals result in LED driver 100 driving the various LEDs to dynamically output known patterns of pleasing color combinations, combinations in which the color and intensity will vary smoothly and gradually over some predetermined period, for example about a minute.

Thus, a viewer seeing night light 10 is treated to a pastel of smoothly and continuously changing color patterns. The light display may start out with a deep blue color that gradually becomes bluish-purple, then a lavender pink color that gradually becomes a red-orange color. The red-orange color gradually becomes a deep red-pink color that gradually becomes a light purple color that gradually becomes a blue color, and then back to a deep blue color, whereupon the cycle will repeat.

The visual effect is both pleasing and comforting, and may promote sleep including promoting sleep for young children. Sufficient light is output to serve the purpose of a night light, yet the output light is not a monotonous flashlight-like monotone but a dynamic kaleidoscope of colors that gradually and pleasingly changes in appearance.

At any time the user may press switch S1, which causes MCU 110 to freeze at the present instruction within instruction set 120. This in turn causes MCU 110 to freeze at the present combination of output signals that are coupled to LED driver 100. The result is the red, green, and blue LEDs will remain driven with the desired, now frozen, pattern of signals, and will output whatever color combination the user found pleasing at the moment switch S1 was pressed or otherwise activated.

At some later time the user may again press S1, which will enable MCU 110 to resume its normal instruction set, which in turn will again cause LED driver 100 to cause the LED array 30 to output a changing set of light patterns. If desired, MCU 110 could be programmed such than when S1 is pressed to "unfreeze" previously "frozen" pattern, the next instruction within MCU 110 will be the initial rather than the next instruction in the instruction set.

Although the present invention has been described with a light array comprising three LEDs, more or fewer LEDs may be used. If desired, LEDs that output different colors when driven with appropriate drive signals may be used. Indeed, light sources other than LEDs may be used, e.g., incandescent bulbs with different colored filters.

Modifications and variations may be made to the disclosed embodiments without departing from the subject and spirit of the invention as defined by the following claims.

What is claimed is:

1. A night light, comprising:
    a housing containing spaced-apart male AC prongs, adapted to mate with an AC socket providing AC operating potential;
    an array of light sources, disposed within said housing, able to emit continuously changing patterns of differently colored light;
    means for driving said array of light sources, disposed within said housing to produce said continuously changing patterns of differently colored light, said means for driving; and
    a control that freezes said continuously changing patterns of differently colored light, such that the night light displays a static pattern of light.

2. The night light of claim 1, wherein said means for driving includes:
    a microcontroller programmed to execute a sequence of operations; and
    a driver unit, coupled to receive at least one output from said microcontroller unit, and coupled to drive said array of light sources responsive to output from said microcontroller.

3. The night light of claim 1, wherein said array of light sources includes at least one light emitting diode (LED).

4. The night light of claim 1, wherein said array of light sources includes at least two of a red light emitting diode (LED), a blue LED, and a green LED.

5. The night light of claim 1, further including a light diffuser, attachable to said housing, through which at least some light emitted by said array is viewable by a user.

6. The night light of claim 1, further including an AC:DC rectifier, coupled to receive raw AC from said spaced-apart male AC prongs, and to deliver DC to at least one of said light array, and said means for driving.

7. The night light of claim 1, wherein said means for driving controls at least one parameter selected from a group consisting of (a) duty cycle of a drive signal coupled to a light source in said array, (b) repetition of an on-portion of a drive signal coupled to a light source in said array, and (c) relative amplitude of a drive signal coupled to a light source in said array.

8. The night light of claim 1, further including a user-operable ON-OFF switch controlling delivery of AC operating potential to said night light.

9. The night light of claim 1, further including a light sensor, disposed within said housing to sense ambient light, to permit delivery of AC operating potential to said night light as a function of sensed said ambient light.

10. A night light, comprising:
    a housing containing spaced-apart male AC prongs, adapted to mate with an AC socket;
    an array of light sources, disposed within said housing, able to output continuously changing patterns of differently colored light;
    a microcontroller-controlled driver unit, disposed within said housing and coupled to deliver drive signals to said array of light sources to produce said continuously changing patterns of differently colored light;

a control that freezes said continuously changing patterns of differently color light such that the night light displays a static pattern of light.

11. The night light of claim 10, wherein said array of light sources includes at least two of (a) a red colored light source, (b) a blue colored light source, and (c) a green colored light source.

12. The night light of claim 10, wherein said array of light sources includes at least two of (a) a red colored light emitting diode (LED), (b) a blue colored LED, and (c) a green colored LED.

13. The night light of claim 10, wherein said array of light sources includes a red colored light emitting diode (LED), a blue colored LED, and a green colored LED.

14. The night light of claim 10, further including an ON/OFF switch use by a user to turn said night light ON and OFF.

15. The night light of claim 10, further including a light sensor responsive to ambient light adjacent said night light, an output of said light sensor turning said night light ON and OFF.

16. The night light of claim 10, further including an AC:DC power supply, coupled to convert AC voltage present at said male AC prongs to DC voltage used by said night light.

17. A method of providing a night light outputting a dynamic display of colored light, the method comprising the following steps:

(a) providing a housing having spaced-apart male AC prongs, adapted to mate with an AC socket;

(b) disposing within said housing an array of light sources able to output continuously changing patterns of differently colored light;

(c) creating and coupling to said array drive signals to produce said continuously changing patterns of differently colored light; and (d) enabling a user to freeze the continuously changing patterns of differently color light.

18. The method of claim 17, wherein step (b) includes disposing at least two of (a) a red colored light source, (b) a blue colored light source, and (c) a green colored light source.

19. The method of claim 17, wherein step (c) includes providing a microcontroller programmed to execute a sequence of instructions resulting in said drive signals.

20. The method of claim 19, further including a switch permitting a user to freeze execution of said sequence of instructions by said microcontroller to create a static pattern of light output from said night light.

* * * * *